United States Patent [19]

Rogers et al.

[11] Patent Number: 5,514,358
[45] Date of Patent: May 7, 1996

[54] METHOD FOR THE SYNTHESIS OF CHEMICAL COMPOUNDS

[76] Inventors: Charles J. Rogers, 4191 Miami Trail La., Cincinnati, Ohio 45252; Alfred Kornel, 3640 Erie Ave., Cincinnati, Ohio 45208

[21] Appl. No.: 412,799

[22] Filed: Mar. 29, 1995

Related U.S. Application Data

[62] Division of Ser. No. 191,504, Feb. 4, 1994.
[51] Int. Cl.$^6$ .............................. C01C 1/00; C01C 1/08; C07C 45/00; C07C 47/02
[52] U.S. Cl. .......................... 423/352; 423/358; 564/448; 564/449
[58] Field of Search .................... 423/359, 659, 423/352, 564, 305, 408, 358; 208/262.5, 262.1, 13; 570/226, 227, 228; 564/448, 449

[56] References Cited

U.S. PATENT DOCUMENTS

| | | | |
|---|---|---|---|
| 2,322,258 | 6/1943 | Strosacker et al. | 570/228 |
| 5,019,175 | 5/1991 | Rogers et al. | 585/641 |
| 5,064,526 | 11/1991 | Rogers et al. | |
| 5,143,710 | 9/1992 | Sawyer et al. | |

OTHER PUBLICATIONS

Transfer Hydrogenolysis of Aryl Halides and Other Hydrogen Acceptors by Formate Salts in the Presence of Pd/C Catalyst, Harold Wiener et al., J. Org. Chem. 1991, 56 pp. 6145–6148.

Catalytic Exchange of Alkylbenzenes with Deuterium on Nickel Films, E. Crawford et al., Trans. Faraday Soc., 58 pp. 2452–2467 (1962).

Stereocontrolled Formation of Cis and Trans Ring Junctions in Hydrindane and Decalin Systems by Palladium–Catalyzed Regioselective and Stereospecific Hydrogenolysis of Allylic Formates, Tadakatsu Mandai et al., J. Org. Chem. 1991, 57 pp. 1326–1327.

Heterogenous Catalytic Transfer Hydrogenation and its Relation to Other Methods for Reduction of Organic Compounds, Robert Johnstone et al., Chem. Rev. 1985, 85, pp. 129–170.

Palladium–Catalyzed Reductions of $\alpha\beta$–Unsaturated Carbonyl Compounds, Conjugated Dienes, and Acetylenes with Trialkylammonium Formates, Nicholas, A. Cortese et al., J. Org. Chem. vol. 43, No. 20, 1978, pp. 3985–3987.

Application of Aqueous Formate Salts as Hydrogen Donors in Reduction Processes: A Techno–Economic Comparison with Pressurized and Elecrically Generated Hydrogen Gas, H. Wiener et al., Int. J. Hydrogen Energy, vol. 14, No. 6, pp. 365–379.

A New Synthesis of Biaryls From Aryl Halides Using Aqueous Alkaline Sodium Formate with Palladium on Charcoal and Surfactant as Catalyst, Peter Bamfield et al., Synthesis, Jul. 1978, pp. 537–538.

*Primary Examiner*—Wayne Langel
*Attorney, Agent, or Firm*—Dinsmore & Shohl

[57] ABSTRACT

Methods for synthesis of chemical compounds by catalytic transfer hydrogenation comprise forming a mixture of a starting material, a hydrogen donor material and a catalyst. The catalyst is selected from a catalytic form of carbon, a polyethylene glycol phase transfer agent, and mixtures thereof. The mixture is heated at a temperature of from 30° to 400° C. in the presence of at least one alkali or alkaline earth metal compound to cause reduction of the starting material by catalytic transfer hydrogenation and form the desired chemical compound product.

15 Claims, No Drawings

METHOD FOR THE SYNTHESIS OF CHEMICAL COMPOUNDS

This application is a division of application Ser. No. 08/191,504 filed Feb. 4, 1994, pending.

FIELD OF THE INVENTION

The present invention relates to methods for the synthesis of chemical compounds using catalytic transfer hydrogenation. More specifically, the present invention relates to methods for the synthesis of chemical compounds by catalytic transfer hydrogenation of a starting material in the presence of a hydrogen donor material, a catalyst and at least one alkali or alkaline earth metal compound.

BACKGROUND OF THE INVENTION

Hydrogenation of unsaturated carbon structures using hydrogen gas and a metal catalyst is a reaction well known to the chemical industry. However, the use of molecular hydrogen poses a serious risk of fire or explosion, with subsequent formation of toxic by-products.

Reduction reactions which employ an organic molecule that functions as the hydrogen donor in the presence of a catalyst are also known in the art and commonly referred to as catalytic transfer hydrogenation methods. The catalytic transfer hydrogenation reaction may be generalized as follows:

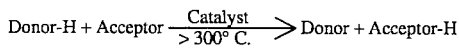

In principle, the donor compound can be any organic compound whose oxidation potential is sufficiently low that hydrogen transfer can occur under relatively mild conditions. For example, at temperatures greater than about 300° C., benzene serves as a hydrogen acceptor and can be reduced to cyclohexane.

Conventional catalytic transfer hydrogenation methods have shown only little commercial potential, generally owing to poor yields and long reaction times, and as a result of the very successful exploitation of the aforementioned methods employing molecular hydrogen with metallic catalysts and hydrides. Cortese et al, *J. Org. Chem.*, 43, 3985 (1978), have disclosed the reductive elimination of halogens from a number of halogenated compounds employing triethylammonium halogens, a temperature of 100° C., triethylammonium formate as a hydrogen donor, a reaction time of 6 hours and a palladium catalyst. While some dehalogenation was achieved, the reaction was incomplete.

Bamfield et al, *Synthesis*, 537 (1978), have disclosed the use of an aqueous alkaline sodium formate solution, a palladium catalyst, a surfactant, a 32 percent hydroxide solution and a temperature of 95° C. to remove halogens from compounds in the synthesis of symmetrical biphenyl. The disclosed reaction resulted in only moderate yields of biphenyl. Wiener et al, *J. Org. Chem.*, 50, 21 (1991) have described methods for catalytic transfer hydrogenation of aryl halides for producing the corresponding arenes. A palladium catalyst effected the transfer hydrogenolysis of the aryl halides using potassium and sodium formate as the hydrogen donor at a temperature of 60° C. and in the presence of an initial amount of water.

In other studies, Crawford et al, *Trans. Faraday Soc.*, 58, 2452 (1962), demonstrated the reduction of alkynes to cis-alkenes by employing molecular hydrogen and palladium catalyst, and Wiener et al have reported on the application of aqueous formate salts as hydrogen donors, *Int. J. Hydrogen Energy*, 14, pp 365–370 (1989).

Most of the elements that have proved to be valuable catalysts for catalytic transfer reductions ate a part of the second transition series in the periodic table. Salts and complexes of Pd, Pt, Ru, Ir, Rh, Fe, Ni, and Co, and particularly of palladium, have all been used primarily as heterogeneous catalysts. The most active catalysts reported for heterogeneous transfer reduction are based on palladium metal. However, the transition series metal catalysts employed in typical catalytic transfer hydrogenation reactions are costly, and new technology must be developed and implemented for their recovery. Strenuous efforts have been undertaken to find catalysts from less expensive metals for use in catalytic hydrogen transfer reduction reactions.

Thus, if catalytic transfer hydrogenation methods are to be effective for the synthesis of chemical compounds, they must be able to employ low cost hydrogen donors and low cost, non-toxic catalysts which do not require extensive recovery treatment. Additionally, the methods must reduce synthesis time as compared with existing catalytic transfer hydrogenation processes, and they must produce high yields of the desired products. It would also be advantageous for such methods to be effected in pressurized, closed and non-pressurized reaction systems. Thus, a need exists for improved catalytic transfer hydrogenation processes for producing chemical compounds.

SUMMARY OF THE INVENTION

Accordingly, it is an object of the present invention to provide catalytic transfer hydrogenation methods for synthesizing chemical compounds. It is a further object of the present invention to provide catalytic transfer hydrogenation methods for synthesizing chemical compounds, wherein the methods employ low cost hydrogen donors and low cost, non-toxic catalysts which do not require extensive recovery treatment. It is a further object of the present invention to provide catalytic transfer hydrogenation methods which require reduced synthesis time and provide increased yields of the desired chemical compound products, particularly as compared with prior catalytic transfer hydrogenation processes. It is also an object of the present invention to provide catalytic transfer hydrogenation methods which may be effected in pressurized, closed and non-pressurized reaction systems.

These objects are achieved by various embodiments of the present invention. Specifically, the present invention relates to methods for the synthesis of chemical compounds by catalytic transfer hydrogenation. The methods comprise providing a mixture of a starting material, a hydrogen donor material and a catalyst selected from a catalytic form of carbon, a polyethylene glycol phase transfer agent, and mixtures thereof, and heating the mixture at a temperature of from 30° to 400° C. in the presence of at least one alkali or alkaline earth metal compound to cause reduction of the starting material by catalytic transfer hydrogenation and form the desired chemical compound products. It has been discovered that the combination of a hydrogen donor material and a catalyst selected from a catalytic form of carbon, a polyethylene glycol phase transfer agent, and mixtures thereof, in combination with heating in the presence of at least one alkali or alkaline earth metal compound causes catalytic transfer hydrogenation reduction of a starting material under relatively mild conditions and forms desired chemical compound products in high yields. The present methods are advantageous in avoiding the use of the metal catalysts which are employed in conventional catalytic transfer hydrogenation reduction reactions and which are costly and difficult to recover.

These and additional objects and advantages provided by the present invention will be further understood in view of the following detailed description.

DETAILED DESCRIPTION

The methods according to the present invention are directed to the synthesis of a chemical compound by catalytic transfer hydrogenation of a starting material. A mixture of the starting material, a hydrogen donor material and a catalyst selected from a catalytic form of carbon, a polyethylene glycol phase transfer agent and mixtures thereof are heated in the presence of at least one alkali or alkaline earth metal compound. Temperatures of from 30° to about 400° C. are employed in the heating step. The starting material is reduced by a catalytic transfer hydrogenation reaction and one or more desired chemical compound products are produced.

The starting material which is employed in the methods of the present invention may be either an organic or inorganic material. The particular selection of a suitable starting material will of course depend on the chemical compound which is to be produced. As will be described in further detail below, nitrogen-containing materials may be employed as starting materials for the production of amines and/or ammonia. Coal, oil, shale, heavy oil, polymers and other fossil fuel precursors and products may be employed as starting materials, particularly in the production of gases, including ammonia, hydrogen sulfide and light aliphatic compounds, aromatic hydrocarbons, phenols, aryl amines and heterocyclic compounds. In other embodiments of the present methods, the starting material may comprise a metal containing compound such as a hydroxide, carbonate or sulfonate and may be used to produce products such as metal oxides, hydrides, carbides or sulfides. In another embodiment of the present methods, the starting material may comprise a halogenated aliphatic compound and the chemical compound which is produced by the catalytic transfer hydrogenation reaction may comprise either a halogenated or non-halogenated product. A particularly preferred example employing a halogenated aliphatic compound as a starting material is a method for the catalytic transfer hydrogenation of ethylene dichloride, wherein vinyl chloride monomer is the resultant product.

The hydrogen donor material which is employed in the methods of the present invention provides hydrogen ions for the reduction reaction of the starting material effected by the catalytic transfer hydrogenation mechanism. The hydrogen donor compound may comprise any hydrogen bearing material under the appropriate reaction conditions. Example of suitable hydrogen donor materials include crude and waste oil, polymers, waste plastics and coal, organic compounds, hydrogen gas and the like. Preferred hydrogen donor compounds include high boiling polar or nonpolar solvents, including fatty acids, aliphatic alcohols or hydrocarbons, amines and the like. In one embodiment, the hydrogen donor material may be modified to effect easier release of the hydrogen ions, whereby the methods of the invention may be conducted at lower temperatures. For example, the hydrogen donor material may be treated with an alkylating agent which can produce tertiary hydrogen atoms in the modified hydrogen donor compound. The tertiary hydrogen atoms are more easily releasable to form hydrogen ions, whereby the methods may be conducted at lower temperatures. The hydrogen material is employed in an amount sufficient to provide the molar amount of hydrogen ions necessary for the desired reduction of the starting material.

In order to activate the hydrogen donor material to produce free radical hydrogen atoms, a catalyst is employed. In accordance with an important feature of the present invention, the catalyst is selected from a catalytic form of carbon, a polyethylene glycol phase transfer agent, and mixtures thereof. One example of a carbon source which is water soluble and suitable for use in the present methods comprises a carbohydrate, for example sucrose. Another example of a carbon source suitable for use in the present methods comprises carbon black, or other carbon source having a relatively large surface area. In the alternate embodiment wherein the catalyst comprises a polyethylene glycol phase catalyst, the polyethylene glycol may be of a molecular weight selected from a wide range, i.e. from about 50 to 20,000 Daltons or more. A preferred polyethylene glycol phase catalyst comprises tetraethylene glycol. In a further embodiment, the catalyst comprises a combination of a carbon source and a polyethylene glycol phase catalyst. The catalyst is employed in the present methods in an amount sufficient to activate release of hydrogen from the donor material and effect the desired hydrogenation reduction reaction to form the chemical compound product.

The mixture of the starting material, hydrogen donor material and catalyst is heated at a temperature from 30° to 400° C. in the presence of at least one alkali or alkaline earth metal compound. The alkali or alkaline earth metal compound may comprise, for example, a carbonate, bicarbonate, oxide or hydroxide, or a compound which generates a carbonate, bicarbonate, oxide or hydroxide. The alkali or alkaline earth metal compound may be employed in the mixture in an aqueous solution or in a high boiling solvent. Alternatively, the alkali or alkaline earth metal compound may be included in the form of a solid dispersion or suspension. If the alkali or alkaline earth compound is added in a high boiling solvent, suitable solvents have a boiling point of at least 100° C., and more preferably from about 200° to about 500° C. Preferred solvents include hydrocarbon compounds. In an additional embodiment, the alkali or alkaline earth metal compound may be employed in an aqueous solution, wherein the aqueous solution further contains a high boiling solvent.

The alkali or alkaline earth metal compound, for example, a carbonate, bicarbonate, oxide or hydroxide, is employed in a molar ratio of from about 1:1 to about 10:1, with respect to the starting material. The specific amount of alkali or alkaline earth metal compound which is required is dependent on the specific starting material and desired product. Any of the alkali and alkaline earth metals, or mixtures thereof, may be employed in the methods of the invention. Preferred alkali metals include lithium, sodium and potassium, with sodium and potassium being particularly preferred.

The alkali and alkaline earth metal carbonates, bicarbonates and oxides may be preferred for use in certain systems owing to their lower toxic effects as compared with alkali and alkaline earth metal hydroxides. However, the hydroxide and oxide compounds are preferred for use in systems where the starting material is acidic in nature or comprises a hydrocarbon material.

In one embodiment, an alkali metal compound is used in combination with an alkaline earth compound. More particularly, the alkali metal compounds are preferred to initiate the catalytic transfer hydrogenation reduction reaction. However, alkali metal compounds are generally more expensive than alkali earth metal compounds. Accordingly, the alkaline earth metal compounds, for example alkaline earth metal oxides, may be used in combination with the alkali metal compound to provide stoichiometric amounts of cations for reaction with the anions liberated from the starting material. When the alkali metal compound and the alkaline earth metal compound are used in combination, the alkaline earth metal compound also absorbs indigenous and chemically formed water in the reaction mixture. Accordingly, less of the more costly alkali metal compound may be used in combination with an alkaline earth metal compound to effect the chemical compound synthesis at a lower cost for raw materials.

As is demonstrated in Example 2 hereafter, an alkali or alkaline earth metal compound may also be used as the starting material in the present methods.

The heating step which is employed in the present methods may be conducted at a temperature between 30° and about 400° C. depending on the starting material and hydrogen donor materials employed, and the desired chemical compound product. In some embodiments, a temperature in the range of from about 50° to about 150° C. is preferred while in other embodiments, a temperature in the range of from about 300° to about 350° is preferred. In still another embodiment, a relatively low temperature in the range of up to about 40° C. is preferred. The examples set forth herein provide additional teachings which will assist one of ordinary skill in the art in selecting the appropriate temperature range to be employed with particular starting materials, and hydrogen donor materials. The heating may be provided by an external heat source, or by initiation of an exothermic reaction.

Depending on the composition of the starting material, the hydrogen donor material and the catalyst, the mixtures which are employed in the present invention may be in the form of an aqueous solution, an organic solvent solution or a solid dispersion or suspension.

The following examples are presented in order to further demonstrate specific embodiments of the invention. Throughout the present specification and examples, parts and percentages are by weight, unless otherwise indicated.

EXAMPLE 1

This example demonstrates the production of amines and ammonia using the catalytic transfer hydrogenation methods of the present invention. Ammonia is synthesized based on the following reaction:

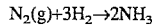

This reaction is highly exothermic and consequently production plants must be carefully designed to control temperatures. Conventional processes are conducted at 100 to 1000 atmospheres and require high temperatures in excess of 500° C. Such processes convert only 5 to 20 percent of the synthesis gases ($N_2/H_2$). Iron catalysts are widely used in conventional ammonia synthesis. However, these catalysts loose their activity when heated to temperatures above 520° C. and are deactivated when in contact with phosphorus, arsenic, sulfur and other contaminants. Thus, in the conventional processes, the synthesis gases must be purified before the ammonia synthesis commences to prevent the catalysts from becoming deactivated.

The process according to the present invention may be used to produce ammonia from a nitrogen bearing material and a hydrogen donor at relatively lower pressures of from 1 to 50 atmospheres. Any nitrogen-containing materials or compounds, including crude deposits of inorganic compounds of nitrogen, may be employed as a starting material in this process. Additionally, numerous hydrogen bearing materials, including crude and waste oils, polymers, waste plastics and coal, can be used as the hydrogen donor material. The catalyst, either a catalytic form of carbon or a polyethylene glycol phase catalyst, or a mixture thereof, is not poisoned or deactivated by high temperatures. Amine compounds may be synthesized according to the same synthesis scheme except that the reaction temperature is controlled, and a base and various solvents including water are introduced into the reaction medium to control the degree of reduction and therefore prevent the amines from being further reduced to ammonia.

In this example, dinitrobenzene is reduced to amine compounds and ammonia. Specifically, a mixture of 100 ml of a hydrocarbon solvent, 20 ml of water, 9.0 g of 2,4-dinitrobenzene, 5.0 g sodium hydroxide and 1.0 g phase catalyst, carbon catalyst mixture was formed. The hydrocarbon solvent served as the hydrogen donor material. The mixture was agitated by stirring and heated to 50° to 100° C. for 15 to 30 minutes to effect complete reduction of the nitro groups to amines. Heating at higher temperature and/or a longer heating period of the mixture resulted in further reduction of the amine groups to ammonia.

EXAMPLE 2

This example demonstrates the synthesis of an inorganic compound using the catalytic transfer hydrogenation methods of the present invention. In conventional processes, hydrogen is reacted with sodium at temperatures between 200° and 350° C. to produce sodium hydrides. However, hydrogen gas in the presence of metallic sodium poses a great risk of fire and/or explosion. Additionally, at temperatures of from 300° to 385° C., sodium and sodium hydroxide react to produce sodium oxide and hydrides. Sodium monoxide substantially free of sodium and sodium hydroxide is produced by sweeping the reaction zone with an inert gas to remove hydrogen. The present invention offers an alternative method for the production of compounds such as sodium oxide and sodium hydride.

A mixture comprising 40 grams of sodium hydroxide (corrected for moisture), 100 ml aliphatic hydrocarbon solvent, and 1.0 g catalyst was formed and placed in a 200 ml round bottom flask. The flask was equipped with a stirring condenser and a receiver to collect water. The contents of the flask were heated to 300° to 350° C. for 1 hour, after which the water in the receiver was measured and compared to that produced in a similar process which did not employ the catalyst or hydrogen donor. The measured water of 18 g produced from the reaction according to the present invention demonstrated that sodium hydroxide had been reduced to the sodium hydride. The example demonstrates the use of the alkali metal compound as the starting material.

A similar method may be used to prepare other metal hydrides, including potassium, rubidium and cesium hydrides, as well as the alkaline earth metal hydrides at and above the temperature employed for the sodium hydride synthesis disclosed above. These methods may also be employed to reduce calcium carbonate, sulfate and other forms of inorganic compounds to carbides, sulfides or oxides using temperatures significantly lower than those employed in conventional methods for the production of such compounds.

EXAMPLE 3

In the past, coal has been subjected to hydrogenolysis to obtain coal chemicals including gases, hydrocarbons, phenols, aryl amines and heterocyclic compounds. Generally, these processes have employed 300 to 400 percent excess hydrogen gas, temperatures of 840° to 1000° F. and pressures of 4,000 to 6,000 psi to yield higher value aromatics and other byproducts.

In accordance with the methods of the present invention, various chemical compounds, including liquid fuels, may be obtained from coal, oil, shale, heavy oil, polymers, plastics and other fossil fuel precursors and products. As an example, a mixture of 100 ml high boiling point aliphatic oil and 50 g crushed coal (20–30 mesh) was formed. The high boiling point aliphatic oil served as a hydrogen donor material and provided a reaction medium. The oil had a boiling point range of 327° to 410° C. The mixture was placed in a 200 ml round bottom flask equipped with a stirrer and 5.0 g sodium hydroxide and 1 g catalyst (polyethylene glycol phase transfer catalyst, carbon catalyst or a mixture thereof) were added. The flask was equipped with a fractionating column and a receiver. The contents of the flask were heated to 350° C. for two hours after which the contents of the flask and receiver were sampled. Products identified from the catalytic transfer hydrogenation reactions of the coal included ammonia, hydrogen sulfide and light aliphatic gases, aromatic hydrocarbons, phenols, aryl amines and heterocyclic compounds. Additionally, greater than 50% of the solid treated coal was liquified.

EXAMPLE 4

This example demonstrates the synthesis of chemical compounds from halogenated aliphatics, which compounds may serve as chemical intermediates in the preparation of polymers and the like. The synthesized compounds may be partially dehalogenated or fully dehalogenated. An example of a partially dehalogenated compound prepared according to the present methods is vinyl chloride prepared from ethylene dichloride, while an example of a fully dehalogenated compound prepared according to the present methods is ethylene prepared from ethylene dichloride. These reactions are as follows:

Partial dehalogenation:

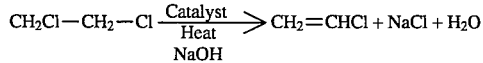

Full dehalogenation:

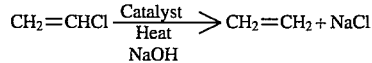

In conventional processes, vinyl chloride monomer is synthesized from ethylene dichloride by thermal dehydrochlorination using a temperature of 500° to 550° C. and a pressure of about 24 atmospheres. The methods of the present invention provide an alternate method for preparing vinyl chloride monomer. Specifically, a mixture of 50 ml hydrocarbon solvent (boiling point range of 100° to 200° C.), 50 g sodium hydroxide, 20 g ethylene dichloride and 1 g polyethylene phase transfer catalyst was formed. The mixture was placed in a 200 ml round bottom flask equipped with a stirrer, a condenser with receiver and a gas collector. The reaction was initiated by the addition of 5–10 ml water or by heating to 30° to 40° C. with stirring in different reaction runs. The conversion of ethylene dichloride to vinyl chloride monomer occurred rapidly with temperature control in a continuous process. It will be apparent that this method is a significant improvement over the prior art method described above.

Ethylene, propylene and other unsaturated chemical intermediates were prepared from partially dechlorinated compounds such as vinyl chloride monomer. The partially dechlorinated starting material was combined in a one liter pressure vessel with 200 ml hydrocarbon, 10 g sodium hydroxide and 1 g of carbon catalyst. The vessel was closed and heated with stirring to a temperature of 280° to 330° C. for one to four hours. After cooling, the contents of the vessel were analyzed and it was determined that only ethylene was present. Similar experiments have demonstrated the synthesis of unsaturated, dehalogenated monomers from halogenated aliphatics for use in various chemical processes.

The preceding examples are set forth to illustrate specific embodiments of the invention and are not intended to limit the scope of the methods of the present invention. Additional embodiments and advantages within the scope of the claimed invention will be apparent to one of ordinary skill in the art.

What is claimed is:

1. A method for the synthesis of an amine compound or ammonia by a catalytic transfer hydrogenation, comprising (a) providing a mixture of a starting material comprising a nitrogen-containing compound, a hydrogen donor material, a catalyst selected from the group consisting of a catalytic form of carbon, a polyethylene glycol phase transfer agent, and mixtures thereof; and (b) heating the mixture at a temperature of from 30° to 400° C. in the presence of at least one alkali or alkaline earth metal compound to cause reduction of the starting material by catalytic transfer hydrogenation and form the amine compound or ammonia.

2. A method as defined by claim 1, wherein the nitrogen-containing compound is an inorganic compound.

3. A method as defined in claim 1, wherein the nitrogen-containing compound is an organic compound.

4. A method as defined by claim 3, wherein the nitrogen-containing compound is dinitrobenzene.

5. A method as defined by claim 1, wherein the hydrogen donor material is selected from the group consisting of organic compounds, polymers and hydrogen gas.

6. A method as defined by claim 1, wherein the hydrogen donor material is selected from the group consisting of fatty acids, aliphatic alcohols, aliphatic hydrocarbons and amines.

7. A method as defined by claim 1, wherein the catalyst comprises a catalytic form of carbon.

8. A method as defined by claim 1, wherein the catalytic form of carbon comprises a carbohydrate or carbon black.

9. A method as defined by claim 1, wherein the catalyst comprises a polyethylene glycol phase transfer agent.

10. A method as defined by claim 1, wherein the catalyst comprises a mixture of a catalytic form of carbon and a polyethylene glycol phase transfer agent.

11. A method as defined by claim 1, wherein the at least one alkali or alkaline earth metal compound is selected from the group consisting of carbonates, bicarbonates, oxides, hydroxides and compounds which generate carbonates, bicarbonates, oxides or hydroxides.

12. A method as defined by claim 1, wherein the heating step is conducted at a temperature in the range of from about 50° to about 150° C.

13. A method as defined by claim 1, wherein the heating step is conducted at a temperature in the range of from about 300° to about 350° C.

14. A method as defined by claim 1, wherein the heating step is conducted at a temperature in the range of up to about 40° C.

15. A method for the synthesis of ammonia by catalytic transfer hydrogenation, comprising (a) providing a mixture of a nitrogen-containing compound, a hydrogen donor material comprising a hydrocarbon solvent, and a catalyst selected from the group consisting of a catalytic form of carbon, a polyethylene glycol phase transfer agent, and mixtures thereof; and (b) heating the mixture at a temperature of from 50° to 150° C. in the presence of at least one alkali or alkaline earth metal compound to cause reduction of the nitrogen-containing compound by catalytic transfer hydrogenation and form ammonia.

* * * * *